United States Patent [19]

Hill

[11] 4,144,744
[45] Mar. 20, 1979

[54] VEIN PREPARATION AND TESTING DEVICE

[75] Inventor: J. Donald Hill, San Francisco, Calif.

[73] Assignee: Thoratec Laboratories Corporation, Emeryville, Calif.

[21] Appl. No.: 835,185

[22] Filed: Sep. 21, 1977

[51] Int. Cl.² ............................................. G01M 3/04
[52] U.S. Cl. ..................................................... 73/49.1
[58] Field of Search ........................ 73/40, 49.1, 49.5; 128/1 R; 138/90

[56] References Cited

U.S. PATENT DOCUMENTS 3,916,874  11/1975  Perrin ................................. 73/49.1 X Primary Examiner—Richard C. Queisser
Assistant Examiner—Joseph W. Roskos
Attorney, Agent, or Firm—Lothrop & West

[57] ABSTRACT

A vein preparation and testing device has a rimmed base forming a shallow basin upstanding from which are a head block and a tail block. In the head block is a removable hollow chuck rotatable about an axis and connected to a liquid reservoir on the base and to a pump. The hollow chuck communicates with a hollow head grip having a tube adapted to lie inside a vein. A fastener holds the vein in place on the tube. In the tail block is a removable tail grip mounted to rotate about the same axis. The tail block is movable along the same axis.

8 Claims, 10 Drawing Figures

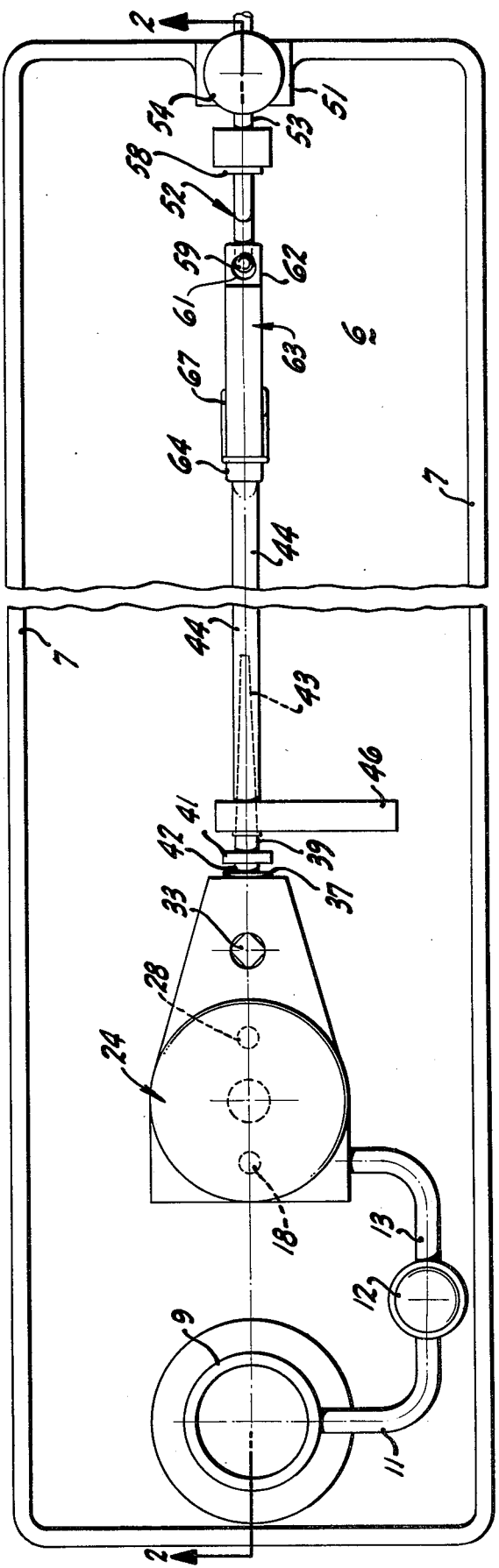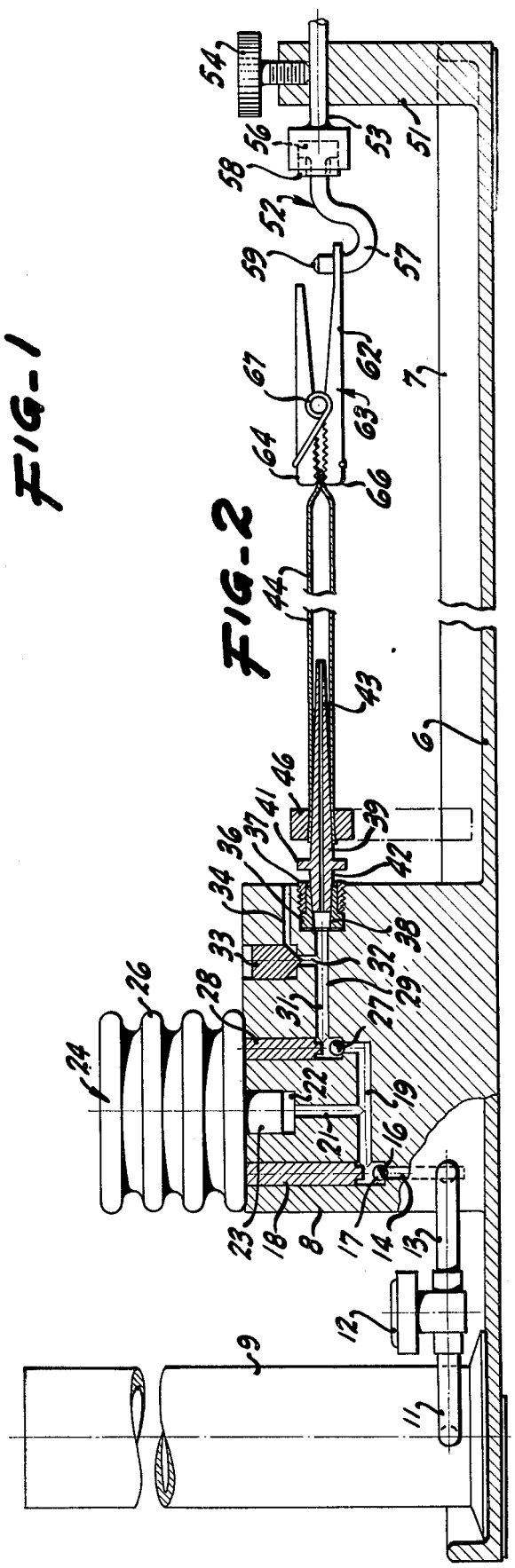

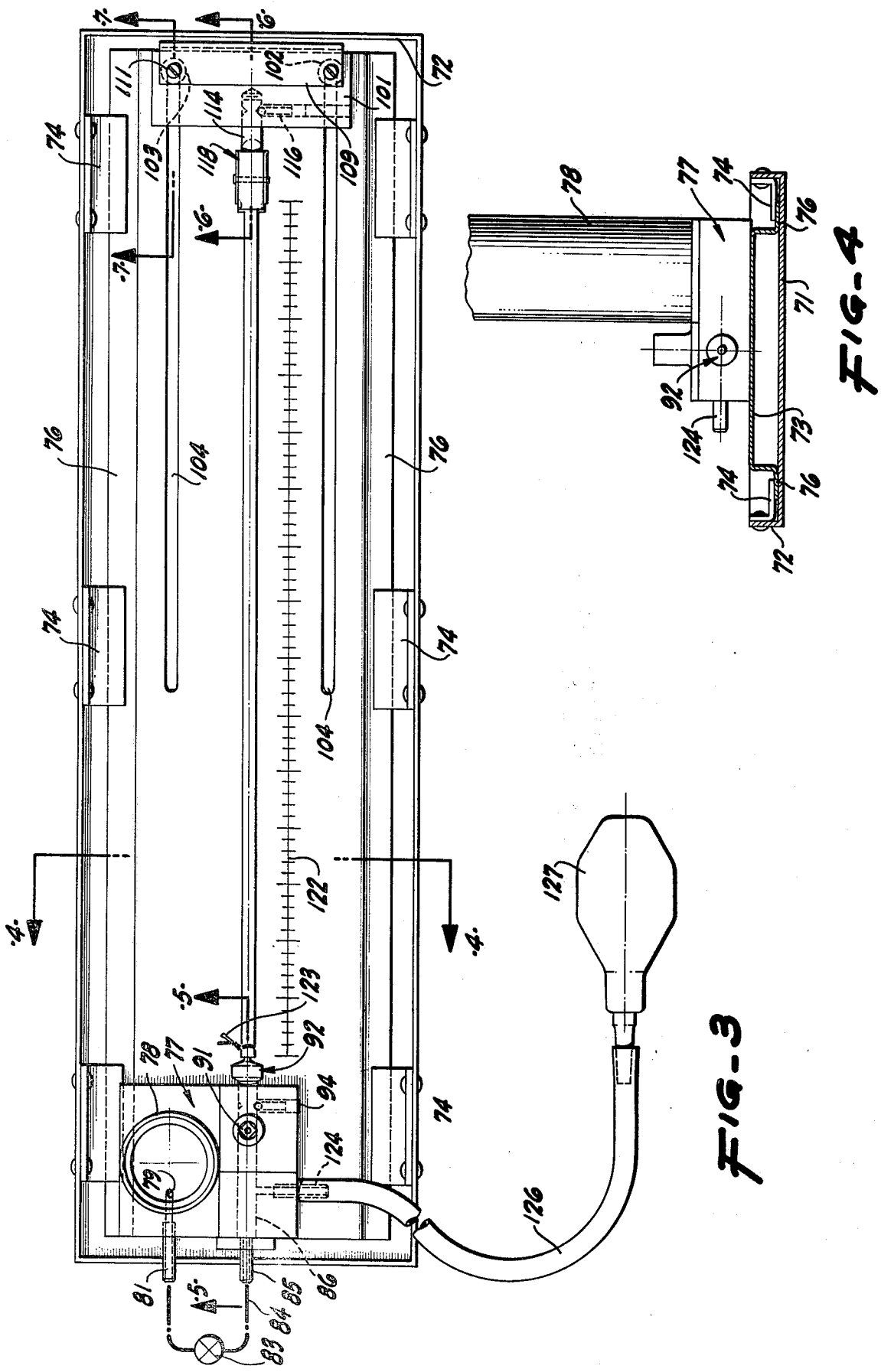

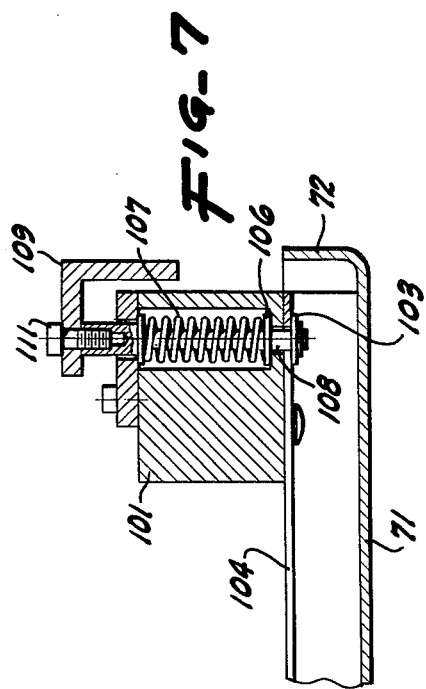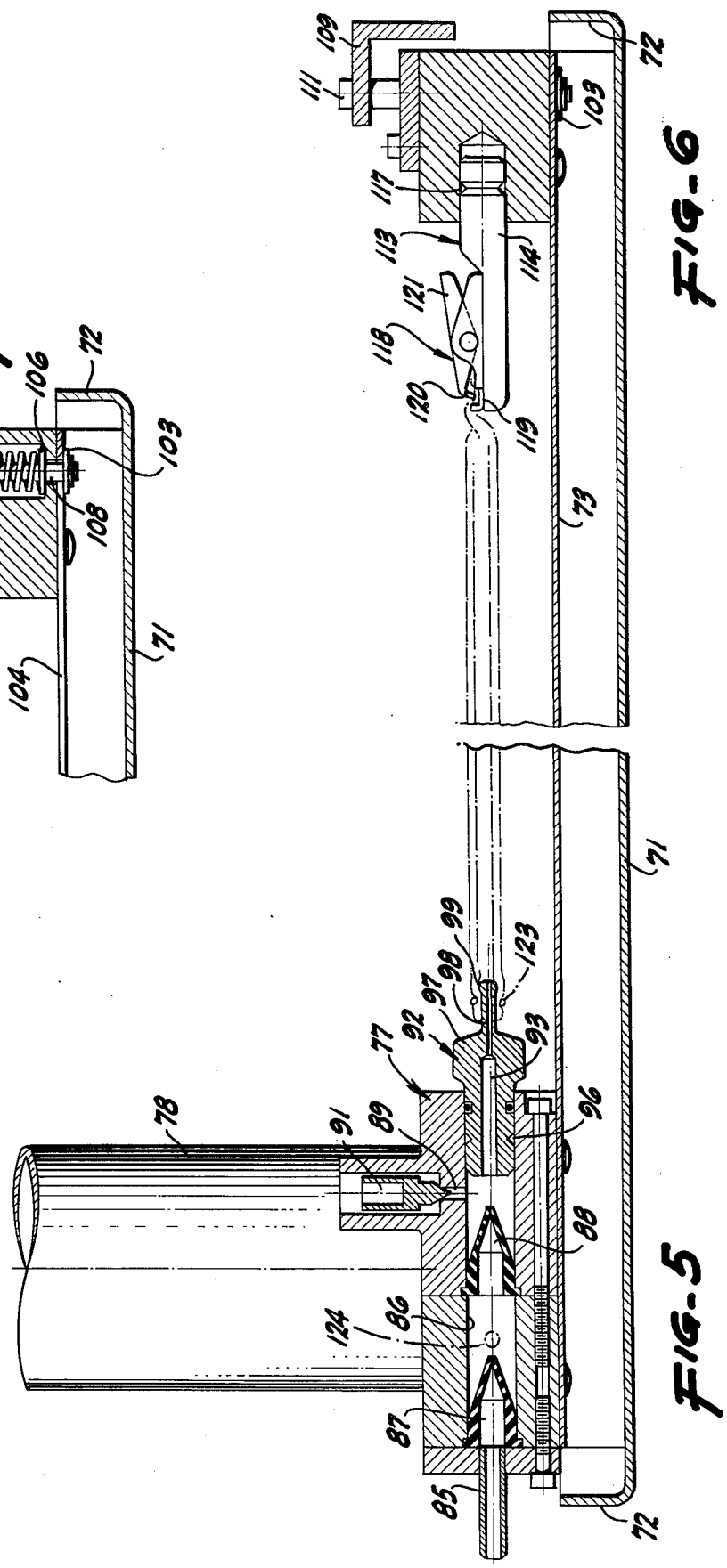

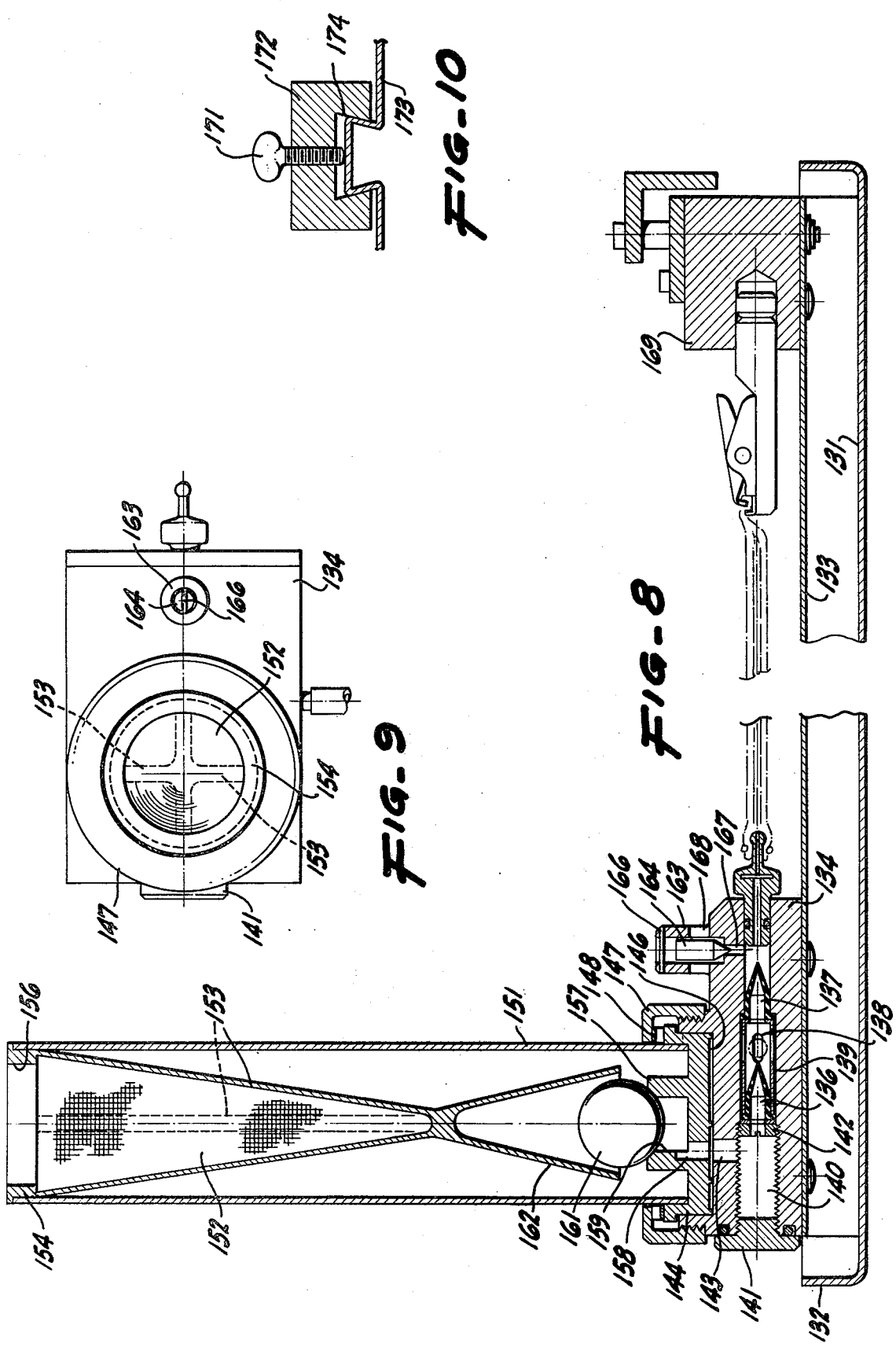

VEIN PREPARATION AND TESTING DEVICE

BRIEF SUMMARY OF THE INVENTION

For employment in preparing and testing a vein section for subsequent use, especially in thoracic surgery, there is provided a base or stand on which the opposite ends of the vein section can be secured. One end of the vein section is at first connected to the hollow chuck and the lumen of the vein irrigated. The vein is then closed at the other end by the tail grip and tested for liquid tightness. The vein is rotated for leak inspection and correction while being internally subjected to liquid under regulated and safe pressure. Any usual length of vein section is quickly mounted in and removed from the testing device.

BRIEF DESCRIPTION OF THE SEVERAL VIEWS OF THE DRAWING

FIG. 1 is a plan, portions being broken away, of one form of the vein preparation and testing device of the invention.

FIG. 2 is a cross-section of the vein preparation and testing device of FIG. 1, the plane of section being indicated by the line 2—2 of FIG. 1, and certain portions of the figure being broken away.

FIG. 3 is a plan, portions being diagrammatic, of another form of vein preparation and testing device of the invention.

FIG. 4 is a cross-section, the plane of which is indicated by the line 4—4 of FIG. 3.

FIG. 5 is a cross-section, the plane of which is indicated by the line 5—5 of FIG. 3.

FIG. 6 is a cross-section, the plane of which is indicated by the line 6—6 of FIG. 3.

FIG. 7 is a cross-section, the plane of which is indicated by the line 7—7 of FIG. 3.

FIG. 8 is a view like FIGS. 2 and 6 but showing a different form of the vein preparation and testing device.

FIG. 9 is a plan of the head block portion of the device of FIG. 8.

FIG. 10 is a detail in transverse, vertical section showing a modified form of tail block mounting.

DETAILED DESCRIPTION

In modern chest surgery, particularly open heart operations, but also in other areas of vascular surgery, there are procedures involving removal of a portion of the patient's vein from another part of the body. In the heart by-pass operations, that vein portion or section is used as a shunt or by-pass around a defective portion of the heart anatomy or its related blood vessels. The excised vein section is customarily of a sufficient length to include a number of collateral veins and may be long enough to serve for more than one shunt or by-pass. While the collateral veins can be readily removed, their removal may nevertheless leave unwanted apertures. The vein must be carefully prepared and checked to ensure there are no unwanted openings or kinks, since in its new location the vein must not leak and must remain internally open. It is therefore important to provide for inspecting and testing the excised vein prior to later use, not only for size and general integrity, but also for the absence of leaks. It is also important to arrange for handling the vein without serious trauma and to facilitate its handling and its repair in the event of a leak. It is desirable to test the vein under a regulated, modest internal pressure, not only to make sure that no leaks are present, but in order to make certain that the vein is appropriate for the intended new site.

Although many variations on the general arrangement are possible, a clinically successful arrangement is as shown in FIGS. 1 and 2 of the accompanying drawings. This embodiment of the device preferably includes a base 6 in the form of a flat pan having an upturned rim 7 all around the edges so that in effect there is afforded a small basin. Upstanding from the base 6 is a head block 8 spaced from one end of the base 6 in order to allow room for an upstanding reservoir 9. This may be a graduate or any other appropriate container customarily simply resting on the base 6 and connected by a tube or pipe 11 through a manual control valve 12 to a pipe 13 entering the head block at a low point.

There is provided a liquid pump largely incorporated in the head block. The pipe 13 is joined to an inlet duct 14 formed in the head block and having a valve seat 16 therein adapted to be opened and closed by a differential pressure responsive inlet check valve 17. The valve is confined in the valve chamber by an after-inserted plug 18 making a tight fit with the head block. From the valve chamber a passage 19 is intersected by a pump duct 21 opening into a pump chamber 22 in which a plunger 23 is reciprocable. The plunger at its upper end is connected to the top of a bellows 24 having corrugated sides 26 and engaging the top of the head block. The passage 19 also has an outlet valve 27 confined to its chamber by a closure plug 28 and affording communication with a passageway 29 symmetrical about a horizontal axis 31. The passageway 29 also opens into a relief passage 32, flow through which is controlled by a combined relief valve and weight 33. From the downstream side of the passage 32, flow is through a relief port 34 to the exterior of the head block, overflow going to the basin 7.

With the arrangement so far described, liquid in the container 9 can be retained in place when the valve 12 is closed, but when the valve 12 is opened, then flow can be partially by gravity into the pump passage 19. The plunger 23 can be manually depressed and withdrawn or can be depressed manually and withdrawn under the influence of a spring, not shown. Flow is then past the outlet check valve 27 into the passage 29. Should the passage 29 be closed downstream, then any resulting excess pressure lifts the valve weight 33 and excess liquid is drained into the pan.

Also mounted in the head block 8 is a hollow chuck 36 retained for rotary motion about the axis 31. The chuck has a conical interior bore 38 and is held for rotary motion by a threaded retainer 37. Designed to be wedged into the bore is a head grip including a hollow conical tube 39 having a manipulating collar 41 thereon. Upstream of the collar 41 is a conical terminus 42 for wedging into the rotary chuck 36 firmly enough to withstand any axial withdrawing force likely to be encountered in vein preparation and testing. Downstream of the manipulating collar, the tube 43 is of considerable axial extent and varies from a small diameter at its free end to a relatively large diameter near the manipulating collar. The tube dimensions are chosen so that the cone will fit snugly into one end of a representative vein section 44. To supplement the frictional holding action between the vein and the head grip, there is provided a clamp 46 similar to a spring-pressed clothespin. This adds a substantial gripping power and is readily placed and removed from the end portion of the vein on the tube 43. The length of the clamp 46 is such that it can easily rotate about the axis 31 without interfering with the base 6.

Also upstanding from the base at a location remote from the head block is a tail block 51. This carries a tail grip 52. The tail grip has a holding rod 53 lined up along the axis 31 and can be variously positioned axially and held in any chosen position by a thumb screw 54. The holding rod 53 is enlarged and socketed to receive the end flange 56 of a transversely engageable hook 57, the flange being retained for rotation about the axis by a thrust ring 58 threaded into position. The hook 57 has a terminus 59 extending transversely of the axis. A transverse movement readily engages the hook 57 with the wall of an opening 61 in one leg 62 of a tail grip clamp 63. This clamp has a pair of jaws 64 and 66 normally urged together by a spring 67.

In the use of this device the vein section 44 has one end telescoped over the head conical tube with the tube on the machine or detached. Care is of course taken so that the conical tube is introduced in a direction so that flow through the tube to the vein can properly continue through the vein in the same direction by opening the internal vein valves. When the vein has been brought far enough onto the conical tube to make a close fit, the clamp 46 is positioned thereover. The conical terminus 42 is frictionally wedged into the rotary chuck 36 in the head block if not already in position.

To expel any air from the vein section, the valve 12 is opened. Liquid in the reservoir 9 flows by gravity through the passage 19, dislodging the check valves 17 and 27, and washes through the vein, escaping from the free end to the basin. This charges the vein section with liquid only. The pump bellows 24 can be reciprocated a few strokes if the liquid level is low or if a higher liquid pressure and velocity are desired, always within the limit imposed by the relief valve 33.

Following that, the other end of the then air-free vein is clamped closed by the jaws 64 and 66 of the clamp 63. The leg 62 is arranged in engagement with the transverse end 59 of the hook 57. The thumb screw 54 is loosened, and the rod 53 is adjusted so as to place the liquid-filled vein 44 under a light tension. This is insufficient to pull the vein from the conical tube or to pull the conical tube from the conical chuck, but is sufficient to maintain the vein in approximately a rectilinear attitude along the axis 31. The thumb screw 54 is then tightened.

When the filled vein has been properly mounted, it is first subjected to the pressure due to the liquid head only and then the pump 24 is actuated to place the vein under a higher liquid pressure, one sufficient to open and disclose any apertures through the walls thereof. These vein openings can be repaired or closed, and by rotating both the manipulating collar 41 and the tail grip 52 the vein section is slowly turned for thorough visual inspection. When the vein shows no further leaks and can withstand the pressure of the pump 24 as set by the relief valve 33, the vein section is available for use. Thereupon, the clamp 63 is released, permitting much of the liquid to flow out, and a portion of the vein that has been clamped in the jaws 64 and 66 is removed, because it may have been traumatized. The vein is then withdrawn from the conical tube 43 after the clamp 46 has been released. That previously clamped portion of the vein is likewise removed, because it likewise may have been traumatized. Any leakage from the vein or liquid overflow or spills are caught in the basin. After use the entire mechanism or parts thereof can be discarded or subjected to sterilization for reuse.

In another, lighter version of the invention, as shown particularly in FIGS. 3 to 7 inclusive, there is provided a base 71 having an upturned margin 72 therearound to afford a basin-like enclosure. Mounted on such base, as particularly shown in FIG. 4, is a removable support channel 73 normally held in position by clips 74 resting against flanges 76 on the margins of the channel 73. Adjacent to one end there is mounted on the channel a head block 77 arranged for ease in manufacture and sterilization.

On the block 77 is a standpipe 78 which may be an attached or a separate reservoir for liquid. A duct 79 extends from the reservoir 78 and has a fitting 81 extending to the exterior. The fitting 81 is connected through a pipe 82 and a valve 83, comparable to the valve 12, to another duct 84 leading to a fitting 85 communicating with a passage 86 in the block. At the entrance to the passage 86 is an inlet valve 87 (FIG. 5), preferably a flattened, open-ended tube of elastomeric material. The valve opens under differential pressure but closes of its own resilience when the differential pressure relaxes. There is an outlet valve 88 of a similar construction in the passageway 86 which opens into a conduit 89 normally closed by a weighted relief valve 91. Flow past the valve 91 when it is open overflows into the basin.

The duct 86 continues past the valve conduit 89 into a combined hollow chuck and tube 92 rotatable in the block 77 about an axis 93 but constrained to that rotation and against axial displacement. This is done by a retainer 94 (FIG. 3) extending into the block and engaging a groove 96 in the tubular chuck 92. The hollow member 92 is thus rotatably retained in the block. The chuck extends axially from the block and its exterior carries a manipulating collar 97 necking down to a hollow tube 98. The tube can be conical, as in FIGS. 1 and 2, or circular cylindrical, and in this instance preferably has a bulbous end 99 thereon.

With this arrangement, the various parts of the mechanism have comparable functions to those previously described, and the tubular chuck 92, although freely rotatable at one end of the basin about the axis 93, is not axially displaceable with regard thereto.

At the other end of the basin, there is provided a tail block 101. In this instance the block 101 is not directly connected to the basin, but rather is connected to the channel 73. The connection involves a pair of friction shoes 102 and 103 adapted to slide under and in close relationship with the upper web of the channel 73, which has a pair of longitudinal or axial slots 104 therein. A washer plate 106 and springs 107 in a cavity in the tail block 101 encompass rods 108 extending through and movable in the slots 104 and engaging the shoes 102 and 103. Under the spring pressure, the tail block is stationary. To release the friction shoes, an angle fitting 109 secured to the rods 108 by screws 111 is depressed, so freeing the shoes 102 and 103 while compressing the springs 107. The fitting is useable in sliding the tail block to a new, fixed position. In this fashion it is possible to set any selected distance between the head block and the tail block.

Mounted in the tail block is a tail grip 113. This includes a circular cylindrical portion 114 rotatable about the same axis 93. The tail grip is retained in axial position by interengagement of a lateral fastening 116 (FIG. 3) with a groove 117 in the cylindrical portion 114.

Set on a flattened portion of the member 114 is a gripper 118 similar to a spring-pressed clothespin and having a lower jaw 119 and an upper jaw 120 normally urged together but capable of being separated by depression of a manual end 121 of the gripper.

In the utilization of this mechanism, the general technique is as has been previously described. If the length of the required vein is previously known, the first operation is to depress the angle plate 109 and axially to move the tail block 101 into an appropriate position, as can be measured by a scale 122 (FIG. 3). The vein at one end is then forced over the bulbous end 99 of the tube 98 and is fastened in position by a binder 123 of a selected kind, so that the vein end is in non-leaking engagement with the tube 98.

The valve 83 is then opened and liquid from the reservoir 78 is permitted to flow by gravity through the valve 87 and into the channel 86 and then through the valve 88 to the interior of the hollow chuck 92. From there flow is into the interior of the vein and continues until all air has been dislodged from the vein interior. The other end of the vein is then introduced into and clamped between the jaws 119 and 120 of the gripper 118. This, being spring-closed, not only holds the vein but also seals it against end leakage. If necessary, the angle plate 109 is again actuated to adjust the distance between the head block and the tail block to afford the desired support or tension to the vein.

Means are provided to get fluid under additional pressure into the interior of the vein. In communication with the passage 86 is a side fitting 124 (FIG. 3) to which is joined a flexible tube 126 going to a hand bulb 127 and with the check valves 87 and 88 in effect forming a pump. By operation of the pump a superior pressure is impressed upon the interior of the vein. There is a limit to this interior pressure since anything in excess of a predetermined amount unseats the valve 91 and any surplus liquid flows out past the valve into the basin.

As the vein is so mounted and is under pressure, it is thoroughly inspected for kinks, for openings, and for general suitability for the purpose. The manipulating collar 97 and the tail grip 113 are rotated as desired so all parts of the vein can be inspected. Any kinks or openings are rectified, and the vein is made fully appropriate for its intended use.

Following that, the manual end 121 of the gripper is released and that releases one end of the vein. The suture 123 is removed and the vein withdrawn or, as an alternative, the suture is left in place and the retainer 94 is withdrawn and the tube 92 and vein removed together. Prior to use as a by-pass, both ends of the released vein are truncated in order to avoid any portion that might have incurred any trauma. The vein is then suitable for use. Under some circumstances, a long vein may intially or finally be cut into several sections in the event more than one by-pass or shunt is required. Such division may be facilitated by the scale 122. After the vein has been removed, the entire mechanism can be discarded or sterilized and made ready for future operations.

The device can be further refined and simplified as shown particularly in FIGS. 8, 9 and 10. While the general layout is the same as in the earlier versions, in this instance there is an especial attempt to avoid expense in manufacture so that under most circumstances an individual device can be utilized once and then discarded without an undue economic penalty. There is also an additional function in the handling of the vein irrigating fluid, as well as changes in some other factors. In this instance there is afforded a shallow basin 131 having an upturned rim 132 and supporting a central channel 133.

To the channel 133 there is affixed a head block 134 within which are fitted valves 136 and 137 arranged either side of a lateral opening 138 leading to a pump bulb like that in FIG. 3 and formed in a tube 139 comparable to the side fitting 124 (FIG. 3).

The supply of liquid to an antechamber 140 ahead of the valve 136 is by a special mechanism. The antechamber end is secured by a removable cap 141 so that the valves 136 and 137 and the intermediate spacer tube 139 are readily insertable and withdrawable upon proper manipulation of a threaded, perforated plug 142. In the block 134 above the chamber 140 there is a passage 143 opening to a base block 144 resting in a cavity 146. The base block is flanged and is held in position by a threaded closure collar 147 resting against a wave washer 148.

Fixed in the base block is an upright tube 151 designed to retain liquid. The container 151 is filled through a conical screen 152 supported on a plurality of radial arms 153 depending from a top flange 154 overlying the upper end of the tube 151. Liquid introduced through the opening 156 travels downwardly through the filter or screen 152 and fills the tube 151.

Particularly to prevent the level of liquid in the tube 151 lowering to such an extent as to allow air to pass into the vein being examined, the base block 144 is provided with a central ring 157 surrounding a compartment 159 from which an eccentric opening 158 communicates with the eccentric opening 143 in one rotated position of the tube 151 relative to the base block. In many other rotated positions of the tube, the opening 158 is out of communication with the opening 143 and flow is then stopped. A buoyant ball 161, when liquid is low or absent, takes a position resting on the ring 157 and stopping downward flow. The ball rises from the ring when surrounded with liquid and so permits flow. The buoyant ball has an upper position against a conical stop 162 integral with the arms 153.

With this mechanism, when the reservoir 151 is empty, the weight of the ball 161 keeps it seated on the ring 157 and no flow can take place around the ball. When liquid is introduced into the reservoir 151, the ball 161 floats upwardly off of the ring 157, so that flow can take place into the valve chamber, but the ball rises only as far as the stop 162. When the liquid level in the chamber 151 descends, the ball 161 falls with it and eventually seats on the ring 157, again precluding flow, while there is still sufficient liquid in the tube 151 to ensure that no air is inducted into and past the valves 136 and 137.

A relief valve is again afforded. The head block 134 has an extension 163 containing a valve needle 164, the upward excursion of which is limited by a cross rod 166. The extension 163 opens into the fluid duct through a passage 167 and to the basin through overflow ports 168.

The vein retaining and clamping structure is approximately as previously described, with a movable tail block 169 substantially the same as shown in FIG. 6, including the angle operator 109. Under some circumstances, however, the tail block is somewhat simplified, as shown in FIG. 10, in that the position retaining mechanism inclusive of the angle operator 109 is replaced by a thumb screw 171 engaging the top of a modified channel 173, the tail block 172 being provided with an interfitting, undercut channel 174. Upon tightening of the thumb screw 171, the tail block 172 is firmly held in any desired axial position.

The technique of using this structure is substantially the same as previously described, but since the structure is simplified, even though having additional features, it can more economically be discarded after a single use. Even so, the simplified design can be easily sterilized for reuse, if desired.

I claim:

1. A vein preparation and testing device comprising a base, a head block upstanding from said base, a hollow head grip including a portion adapted to engage the exterior of a vein, means for mounting said head grip for rotation on said head block about an axis and against displacement along said axis, a tail block upstanding from said base, a tail grip including a portion adapted to engage the exterior of said vein, and means for mounting said tail grip for rotation on said tail block about said axis and against displacement along said axis.

2. A device as in claim 1 including means on said head block and including a stationary passage in said head block for supplying fluid under pressure to said rotary hollow head grip.

3. A device as in claim 1 in which said head grip vein-engaging portion includes a tube extending along said axis and adapted to lie inside a vein, and means adapted to engage the exterior of said vein to clamp said vein on said tube and to rotate with said tube and said vein relative to said base.

4. A device as in claim 1 in which said tail grip vein-engaging portion includes means for engaging and closing the end wall portions of said vein against each other.

5. A device as in claim 4 in which said engaging and closing means is a spring-closed pincer.

6. A device as in claim 1 in which said means for mounting said tail grip includes means for holding said tail grip in various axial locations on said base relative to said head grip.

7. A device as in claim 1 including means for transversely connecting and disconnecting said tail grip relative to said tail block.

8. A device as in claim 1 including means for holding said tail grip in a selected axial position on said base against axial tension imparted to said tail grip through a vein engaged by said tail grip.

* * * * *